United States Patent [19]

Furuya et al.

[11] Patent Number: 5,184,159
[45] Date of Patent: Feb. 2, 1993

[54] LIGHT SOURCE APPARATUS FOR ENDOSCOPE

[75] Inventors: Katsuhiko Furuya; Tadashi Takahashi, both of Tokyo, Japan

[73] Assignee: Asahi Kogaku Kogyo Kabushiki Kaisha, Tokyo, Japan

[21] Appl. No.: 553,600

[22] Filed: Jul. 18, 1990

[30] Foreign Application Priority Data

Jul. 25, 1989 [JP] Japan .................................. 1-193685
Aug. 21, 1989 [JP] Japan .................................. 1-215659

[51] Int. Cl.⁵ .......................................... G03B 29/00
[52] U.S. Cl. ...................................... 354/62
[58] Field of Search ............................ 354/62

[56] References Cited

U.S. PATENT DOCUMENTS

| | | | |
|---|---|---|---|
| 3,742,828 | 7/1973 | Nakajima et al. | 354/421 |
| 4,021,663 | 5/1977 | Takahashi | 250/227.2 |
| 4,222,644 | 9/1980 | Tano et al. | 354/475 |
| 4,306,785 | 12/1981 | Tano et al. | 354/426 |
| 4,322,129 | 3/1982 | Takahashi et al. | 350/269 |
| 4,343,300 | 8/1982 | Hattori | 354/62 X |
| 4,366,529 | 12/1982 | Takahashi et al. | 362/4 |
| 4,487,489 | 12/1984 | Takamatsu | 354/62 |
| 4,561,429 | 12/1985 | Sato et al. | 354/62 X |

FOREIGN PATENT DOCUMENTS 0027263 4/1981 European Pat. Off. .
61-80217 4/1986 Japan .
63-40096 8/1988 Japan .
2137766 10/1984 United Kingdom .

OTHER PUBLICATIONS

English Abstract to Japanese Application 61-80217.

Primary Examiner—Michael L. Gellner
Assistant Examiner—Howard B. Blankenship
Attorney, Agent, or Firm—Sandler, Greenblum & Bernstein

[57] ABSTRACT

A light source apparatus for an endoscope, which has a light source for supplying light for illuminating an object to the endoscope that is equipped with a photographing device. The light source apparatus comprises an exposure control device for controlling the quantity of exposure light applied to a photographic plane in the photographing device, a condition input device for inputting plural various conditions for setting an exposure index which is used to determine the exposure light quantity, and an exposure index setting device for calculating the exposure index from various conditions which are inputted through the condition input device and outputting it to the exposure control device. The exposure index setting device may calculate an exposure index which is required to determine the exposure light quantity, and a device for storing data is used to set the exposure index, which is interchangeably provided with respect to the exposure index setting device.

7 Claims, 16 Drawing Sheets

FIG.3

EXPOSURE INDEX

| | | | | | |
|---|---|---|---|---|---|
| Scope | Pentax | Others. | | | |
| Adapter | 55 | 75 | 105 | | mm |
| Camera | 35 | 110 | Others | | |
| Film | 100 | 200 | 400 | 1000 | 1600 |
| EF | -1 | -0.5 | 0 | 0.5 | 1 |
| Memory | 1 | 2 | 3 | 4 | 5 |

Reset — 47
46
Set — 48

45s Scope
45a Adapter
45c Camera
45f Film
45e EF
45m Memory

FIG. 4

| EXP. VALUE | $2^{+\frac{5}{2}}$ | $2^{+2}$ | $2^{+\frac{3}{2}}$ | $2^{+1}$ | $2^{+\frac{1}{2}}$ | $2^1$ | $2^{-\frac{1}{2}}$ | $2^{-1}$ | $2^{-\frac{3}{2}}$ | $2^{-2}$ |
|---|---|---|---|---|---|---|---|---|---|---|
| EXP. INDEX (EI) | 0 | 1 | 2 | 3 | 4 | 5 | 6 | 7 | 8 | 9 |

FIG.5

$EI = FTs + FTa + FTc + FTf + FTe - 11$

| ENDOSCOPE | TYPE | Pentax | Others |     |     |      |      |      |
|-----------|------|--------|--------|-----|-----|------|------|------|
|           | FTs  | 2      | 2      |     |     |      |      |      |

| ADAPTER | TYPE | 55mm | 75mm | 105mm |
|---------|------|------|------|-------|
|         | FTa  | 6    | 4    | 2     |

| CAMERA | TYPE | 35 | 110 | Others |
|--------|------|----|----|--------|
|        | FTc  | 2  | 2   | 2      |

| FILM | ISO | 25 | 50   | 64 | 100 | 200 | 400 | 1000 | 1600 | 3200 |
|------|-----|----|------|----|-----|-----|-----|------|------|------|
|      | FTf | 2  | 4    | 5  | 6   | 8   | 10  | 13   | 14   | 16   |

| EF | EV  | -1 | -0.5 | 0 | +0.5 | +1 |
|----|-----|----|------|---|------|----|
|    | FTe | -2 | -1   | 0 | 1    | 2  |

FIG.13

| EXP. VALUE | $2^{+\frac{5}{2}}$ | $2^{+2}$ | $2^{+\frac{3}{2}}$ | $2^{+1}$ | $2^{+\frac{1}{2}}$ | 1 | $2^{-\frac{1}{2}}$ | $2^{-1}$ | $2^{-\frac{3}{2}}$ | $2^{-2}$ |
|---|---|---|---|---|---|---|---|---|---|---|
| EXP. INDEX (EI) | 0 | 1 | 2 | 3 | 4 | 5 | 6 | 7 | 8 | 9 |

FIG. 14

$EI = FTs + FTa + FTc + FTf + FTe - 11$

| ENDOSCOPE | TYPE | Pentax | Others | | | | | | | |
|---|---|---|---|---|---|---|---|---|---|---|
| | FTs | 2 | 2 | | | | | | | |

| ADAPTER | TYPE | 55mm | 75mm | 105mm | | | | | | |
|---|---|---|---|---|---|---|---|---|---|---|
| | FTa | 6 | 4 | 2 | | | | | | |

| CAMERA | TYPE | 35 | 110 | Others | | | | | | |
|---|---|---|---|---|---|---|---|---|---|---|
| | FTc | 2 | 2 | 2 | | | | | | |

| FILM | ISO | 25 | 50 | 64 | 100 | 200 | 400 | 1000 | 1600 | 3200 |
|---|---|---|---|---|---|---|---|---|---|---|
| | FTf | 2 | 4 | 5 | 6 | 8 | 10 | 13 | 14 | 16 |

| EF | EV | −1 | −0.5 | 0 | +0.5 | +1 | | | | |
|---|---|---|---|---|---|---|---|---|---|---|
| | FTe | −2 | −1 | 0 | 1 | 2 | | | | |

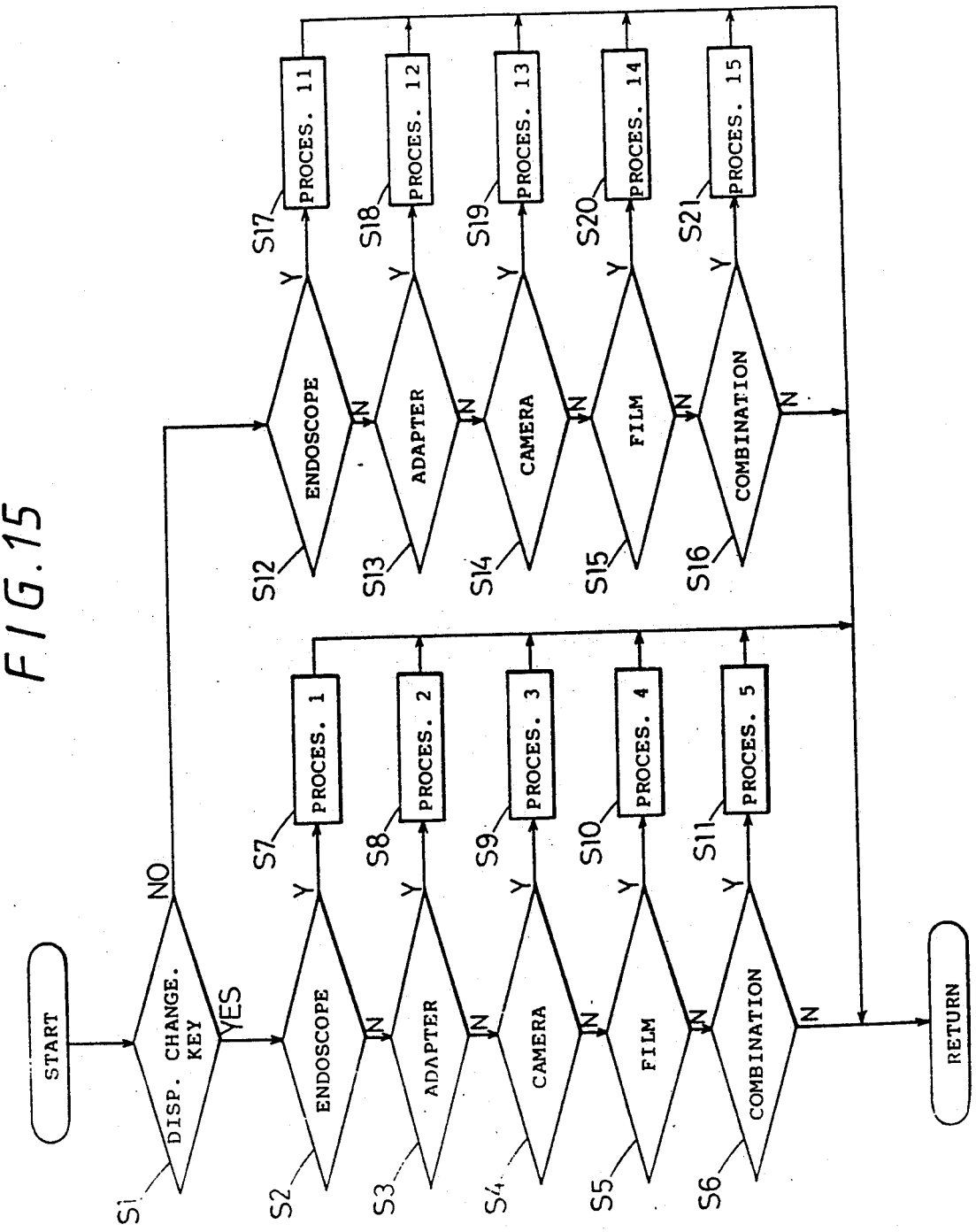

LIGHT SOURCE APPARATUS FOR ENDOSCOPE

BACKGROUND OF THE INVENTION

1. Field of the Invention

The present invention relates to a light source apparatus for an endoscope, which is designed to be capable of automatic exposure control when a photograph is to be taken through the endoscope.

2. Description of the Background and Relevant Materials

To effect automatic exposure control when a photograph is to be taken through an endoscope, it is necessary to change a set reference that is used to determine a correct exposure, that is, an exposure index that is used in automatic exposure control, in accordance with various conditions, for example, the type of endoscope, the magnification of a photographic adapter and the sensitivity of a film, which are employed in the photographing operation.

To meet this need, a typical conventional light source apparatus for an endoscope has heretofore been arranged such that an optimal one of several different exposure indexes can be selected by a manual operation in accordance with a combination of various conditions.

However, the selection of an optimal exposure index in accordance with each particular combination of various conditions necessitates referring to an instruction manual, for example. Therefore, no rapid setting of an exposure index can be performed, and a setting error is likely to occur. If erroneous setting is made, the whole film will be over- or under-exposed.

In addition, in the conventional light source apparatus, the adjustable range of exposure indexes is fixed. Accordingly, when a new type of endoscope or a photographic adapter whose magnification is quite different from those of ordinary ones appears, or when a film whose sensitivity is markedly different from those of ordinary ones is used, an exposure index which is appropriate therefor may be out of the adjustable range. In such a case, it is impossible to set an appropriate exposure index, and the whole film will therefore be over- or under-exposed.

SUMMARY OF THE INVENTION

An aspect of the present invention is a light source apparatus for an endoscope, which is capable of setting an optimal exposure index rapidly and accurately.

Another aspect of the present invention is a light source apparatus for an endoscope, which is capable of setting a proper exposure index at all times, irrespective of the types of devices which are used in the photographing operation.

Other aspects and advantages of the present invention will become apparent from the following detailed description of an illustrated embodiment of the invention.

According to the present invention, there is provided a light source apparatus for an endoscope, which has a light source for supplying light for illuminating an object to the endoscope that is equipped with a photographing device, comprising: an exposure control device for controlling the quantity of exposure light applied to a photographic plane in the photographing device; a condition input device for inputting various conditions for setting an exposure index which is used to determine the exposure light quantity; and an exposure index setting device for calculating the exposure index from various conditions which are inputted through the condition input device and outputting it to the exposure control device.

In addition, there is provided a light source apparatus for an endoscope, which has a light source for supplying light for illuminating an object to the endoscope that is equipped with a photographing device, comprising: a device for storing data which is required to determine the quantity of exposure light applied to a photographic plane in the photographing device, the data storage device being interchangeably provided; a device for reading the data from the data storage device; and an exposure control device for controlling the exposure light quantity using the data which is read by the data reading device.

BRIEF DESCRIPTION OF THE DRAWINGS

The present invention may be more fully understood from the description of a preferred embodiment of the invention set forth below, together with the accompanying drawings, in which:

FIG. 3 is a front view of a panel thereof;

FIG. 4 is a chart showing the relationship between the exposure value and the exposure index in the embodiment of FIG. 1;

FIG. 5 is a chart showing one example of the setting of FT-numbers in the embodiment of FIG. 1;

FIG. 13 is a chart showing the relationship between the exposure value and the exposure index in the second embodiment;

FIG. 14 is a chart showing one example of the setting of FT-numbers in the second embodiment; and FIGS. 15, 16 and 17 are flowcharts showing an exposure index setting control process in the second embodiment.

DETAILED DESCRIPTION OF EMBODIMENT

Figure 1:
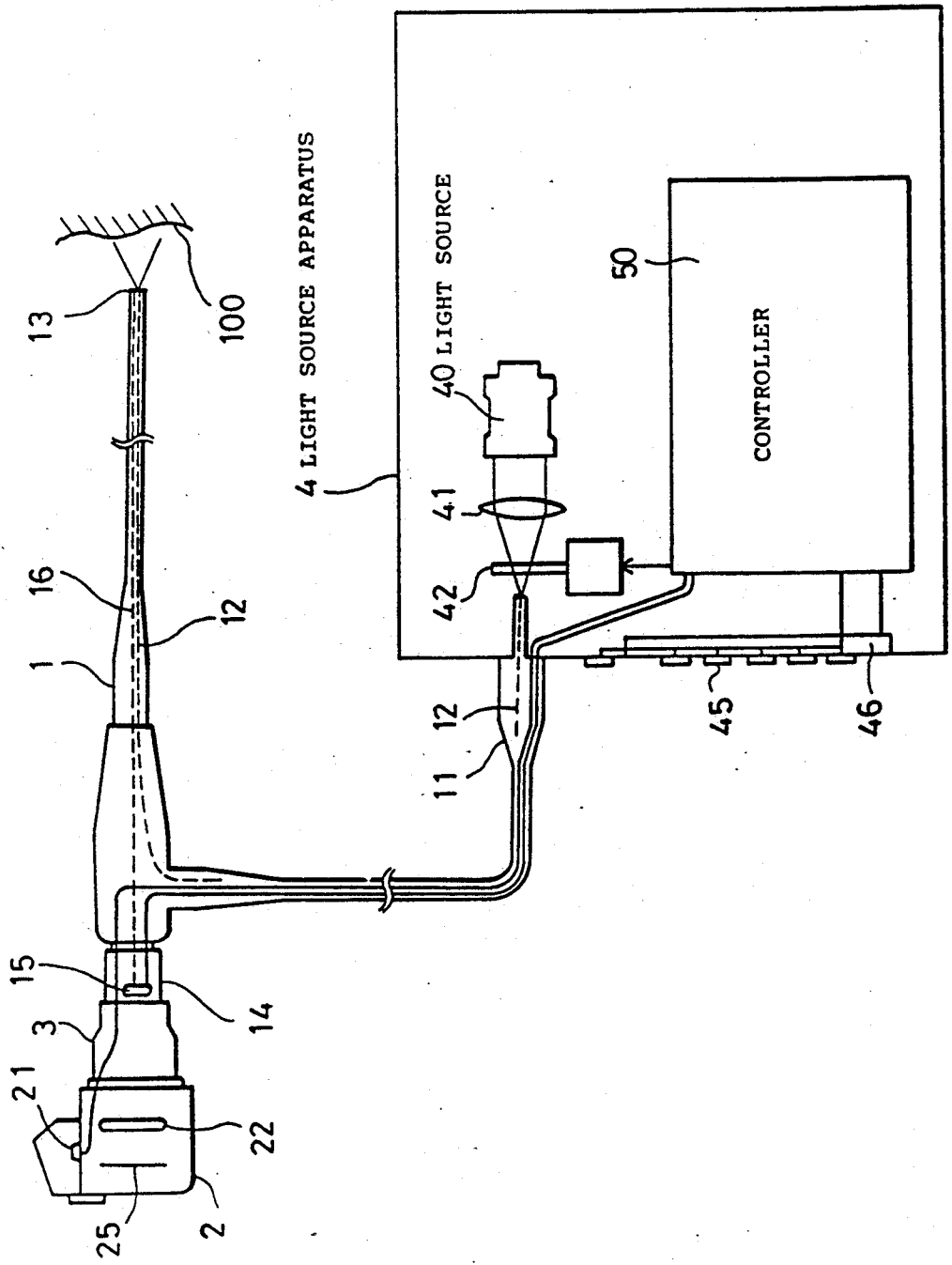
FIG. 1 shows one embodiment of the light source apparatus for an endoscope according to the present invention.

Referring to FIG. 1, reference numeral 1 denotes an endoscope. A camera 2 is detachably attached to an eyepiece 14 of the endoscope 1 through a photographic adapter 3.

Reference numeral 4 denotes a light source apparatus, to which is detachably connected to a connector 11 of the endoscope 1. Illuminating light that is emitted from a light source 40, preferably a lamp, is condensed through a condenser lens 41, transmitted through a light guide fiber bundle 12 in the endoscope 1, and applied to an object 100 from the distal end 13 of an insert part of the endoscope 1. The reflected light from the object 100 is transmitted through an image guide fiber bundle 16 to expose the plane of a film 25 in the camera 2.

The exposure light quantity is controlled by a shutter (light source shutter) 42 which is provided in an illuminating light path inside the light source apparatus 4. A shutter 22 in the camera 2 is opened for a predetermined time, which is preferably about 0.25 sec, when a synchro switch 21 is turned on.

A light-receiving element 15 detects a brightness level of the exposure light that is applied to the plane of the film 25. The output ends of the synchro switch 21 and the light-receiving element 15 are connected to a controller 50 which is provided in the light source apparatus 4. In addition, select switches 45 and a display 46, which are provided on the front panel of the light source apparatus 4, are connected to the controller 50.

Figure 2:
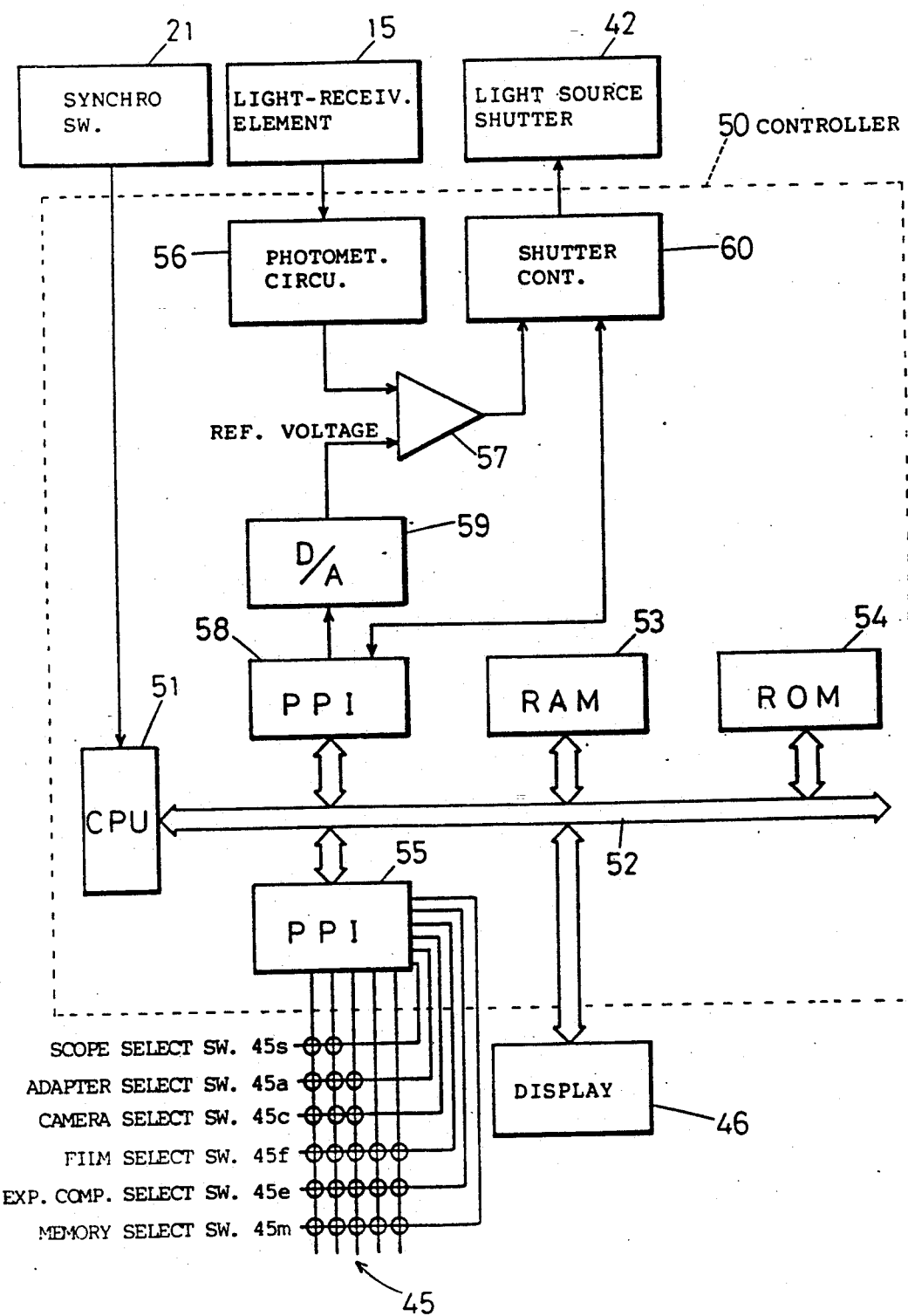
FIG. 2 is a circuit block diagram thereof.

Referring next to FIG. 2, which is a block diagram showing the arrangement of the controller 50, a random access memory (RAM) 53, a read-only memory (ROM) 54, the display 46, and programmable interfaces 55 and 58 are connected to a system bus 52 which is in turn connected to a central processing unit (CPU) 51.

The CPU 51 is supplied with an interrupt signal which is outputted from the synchro switch 21.

The select switches 45 include endoscope select switches 45s, photographic adapter select switches 45a, camera select switches 45c, film select switches 45f, exposure compensation switches 45e and memory select switches 45m, which are connected to the system bus 52 through a first programmable interface (PPI) 55.

An output signal from the light-receiving element 15 is integrated in a photometric circuit 56 and then inputted to one input terminal of a comparator 57. The other input terminal of the comparator 57 is connected to the output terminal of a D/A converter 59 which converts a digital signal to an analog signal. The D/A converter 59 is connected to the system bus 52 through a second programmable interface (PPI) 58. The output terminal of the comparator 57 and the second PPI 58 are connected to a shutter control circuit 60 for controlling the operation of the shutter 42 in the light source apparatus 4.

FIG. 3 shows the display 46 and the select switches 45, which are provided on the front side of the light source apparatus 4.

An exposure index which is to be set is displayed in the upper part of the display 46. Below the exposure index display section are disposed various select switches 45s, 45a, 45c, 45f and 45e for selecting kinds of endoscope, photographic adapter, camera and film, together with an exposure compensation value to be set. Thus, it is possible to readily select various conditions while visually checking the conditions to be selected. Reference numeral 47 denotes a reset switch for setting selected data to respective initial values.

Five memory switches 45m for reading out set conditions stored in the RAM 53 are disposed in the lower part of the display 46. Reference numeral 48 denotes a set switch for storing set conditions in the memory.

It should be noted that in this embodiment, only the memory switches 45m comprise switches which alternate between "on" state and "off" state each time they are depressed, and the other switches comprise switches which are on as long as they are depressed.

FIG. 4 shows the relationship between the exposure value and the exposure index (EI), and FIG. 5 shows one example of the setting of FT-numbers. It should be noted that FT-numbers are integral numbers which are adopted in this embodiment for various kinds of endoscope, photographic adapter, camera, film and exposure compensation value for the purpose of facilitating the calculation of an optimal exposure index, the FT-numbers being set so that an exposure value difference of 1 EV is equivalent to 2 in terms of FT-numbers.

As shown in FIG. 4, the exposure index (EI) for a standard exposure value is determined to be 5, and an exposure value difference of 1 EV is equivalent to 2 in terms of the exposure index (EI).

Assuming that FT-values which are given by endoscopes, photographic adapters, cameras, films and exposure compensation values (EF) are FTs, FTa, FTc, FTf and FTe, respectively, as shown in FIG. 5, then the exposure index EI is given by $$EI = FTs + FTa + FTc + FTf + FTe - 11$$

It should be noted that the data shown in FIG. 5 has been stored in the ROM 54 in advance. Accordingly, if the ROM 54 is interchangeably provided, any exposure index can be set for any new data by supplying the required data from the ROM 54.

Figure 6:
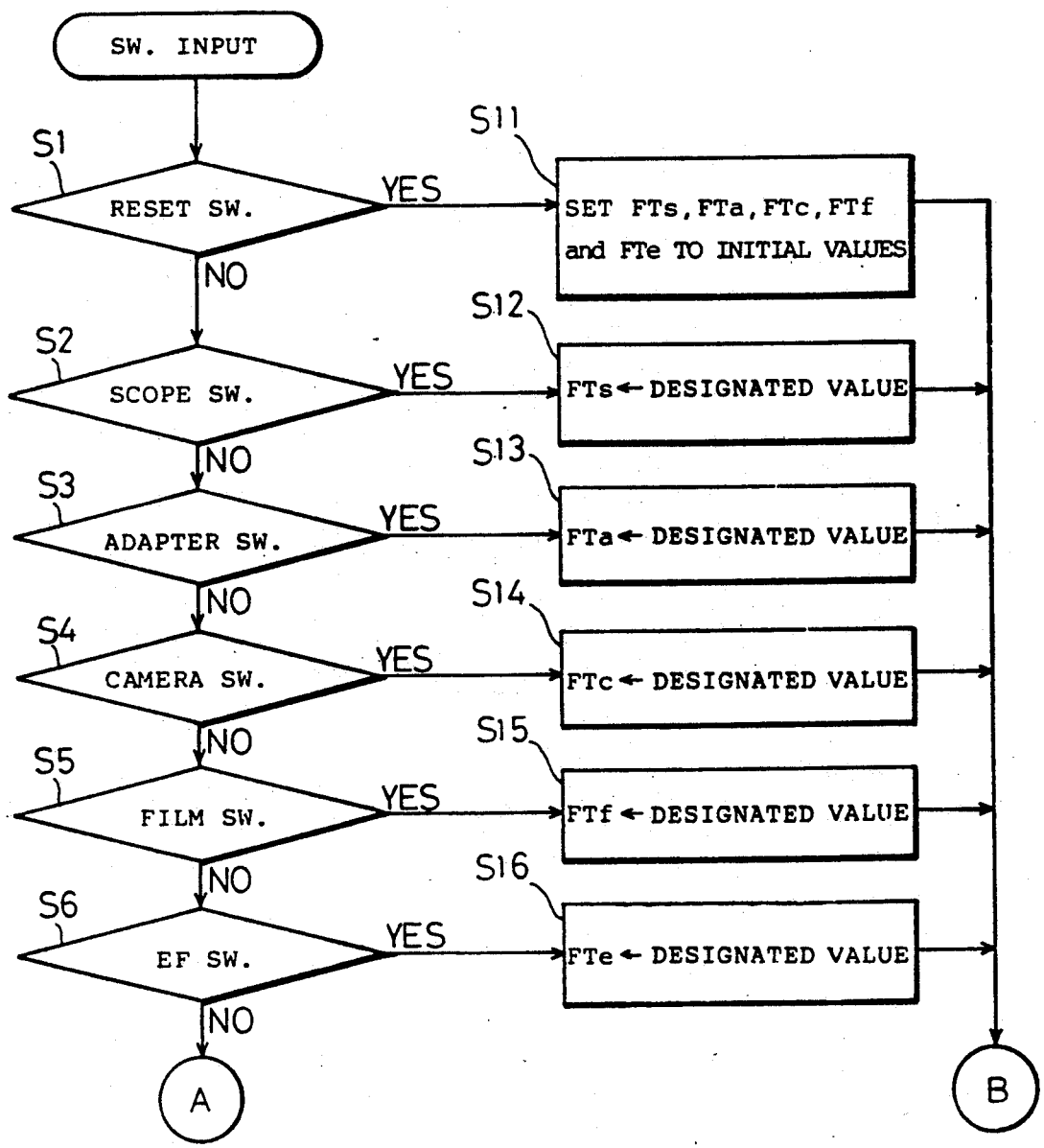
FIGS. 6 and 7 are flowcharts showing an exposure index setting control process in the embodiment of FIG. 1.
Figure 7:
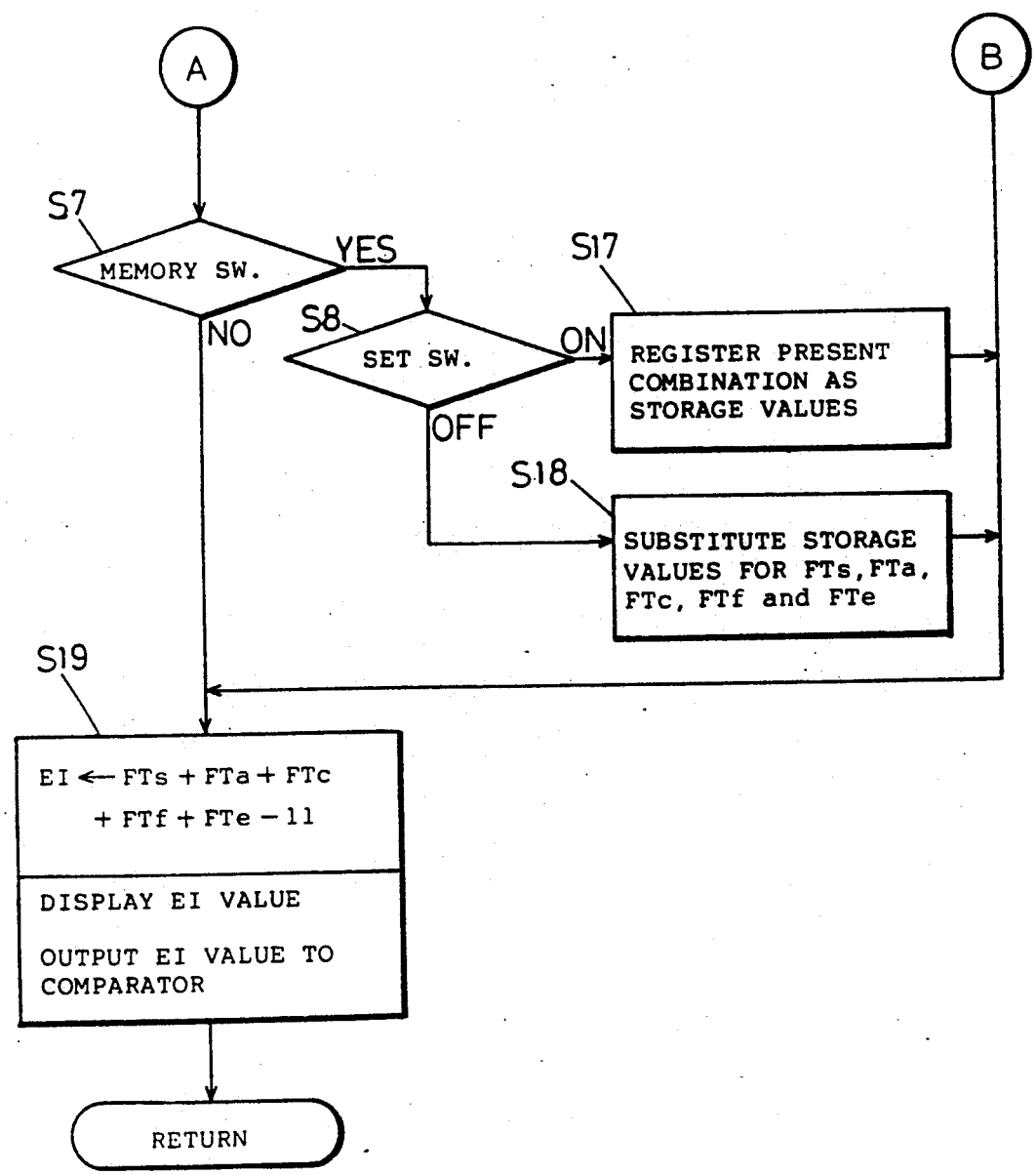

FIGS. 6 and 7 are flowcharts showing an exposure index setting control process that is executed in the controller 50, in which S denotes Step.

This process starts when an input operation is executed by actuating any of the select switches 45, the memory switches 45m or the reset switch 47. It is first judged in S1 whether or not the reset switch 47 has been depressed. If YES, all the FT-numbers are set to the respective initial values in S11, and the process then proceeds to S19, in which an exposure index EI is calculated from these FT-numbers and displayed on the display 46. In addition, the calculated exposure index EI is outputted from the second PPI 58 to the comparator 57 through the D/A converter 59, thus completing this control process.

If it is judged in S1 that any switch other than the reset switch 47 has been depressed, which one of the endoscope select switches 45s, adapter select switches 45a, camera select switches 45c, film select switches 45f and exposure compensation switches 45e has been depressed is judged in S2 to S6.

If it is judged that any of these select switches 45 has been depressed, designated values that are selected through the select switches 45 are substituted for the corresponding FT-numbers in S11 to S16, and the process then proceeds to S19, in which an exposure index EI is calculated from the substituted FT-numbers and displayed on the display 46. In addition, the calculated exposure index EI is outputted from the second PPI 58 to the comparator 57 through the D/A converter 59.

Thus, the operation of the shutter control circuit 60 is controlled on the basis of the exposure index that has been calculated and set as described above, thereby executing automatic exposure control with respect to the plane of the film 25 in the photographing operation.

If it is judged in S1 to S6 that none of the select switches 45 has been depressed, it is then judged in S7 whether or not a memory switch 45m has been depressed. If YES, it is judged in S8 whether or not the set switch 48 is ON.

If the set switch 48 is judged to be ON, a combination of conditions which are presently selected through the select switches 45 is registered as a combination of storage values and stored in the RAM 53 in S17, and the process then proceeds to S19.

If it is judged in S8 that the set switch 48 is not ON, a combination of conditions that have been registered as storage values through one of the memory switches 45m that has been just depressed is read out from the RAM 53, and the readout storage values are substituted for FTs, FTa, FTc, FTf and FTe. Thereafter, the process proceeds to S19, in which an exposure index EI is calculated from the substituted FT-numbers and displayed on the display 46. In addition, the calculated exposure index EI is outputted from the second PPI 58 to the comparator 57 through the D/A converter 59.

Thus, automatic exposure control with respect to the plane of the film 25 is executed on the basis of the exposure index corresponding to the combination that has been registered through one of the memory switches 45m.

According to the present invention, an optimal exposure index is automatically set in accordance with various conditions, for example, a combination of devices and film used, simply by inputting various conditions concerning devices used and the sensitivity of a film employed through the condition input means of the light source apparatus. Thus, setting of an optimal exposure index can be effected readily and without any error and hence a photographing operation can be executed with a correct exposure at all times.

Moreover, since appropriate conditions can be selected from among various conditions which have been previously stored in the memory, the operation of inputting necessary conditions is extremely easy. If the arrangement is such that combinations of various conditions have been stored in advance and a desired one of the stored combination is selected, the condition input operation can be performed instantaneously.

Figure 8:
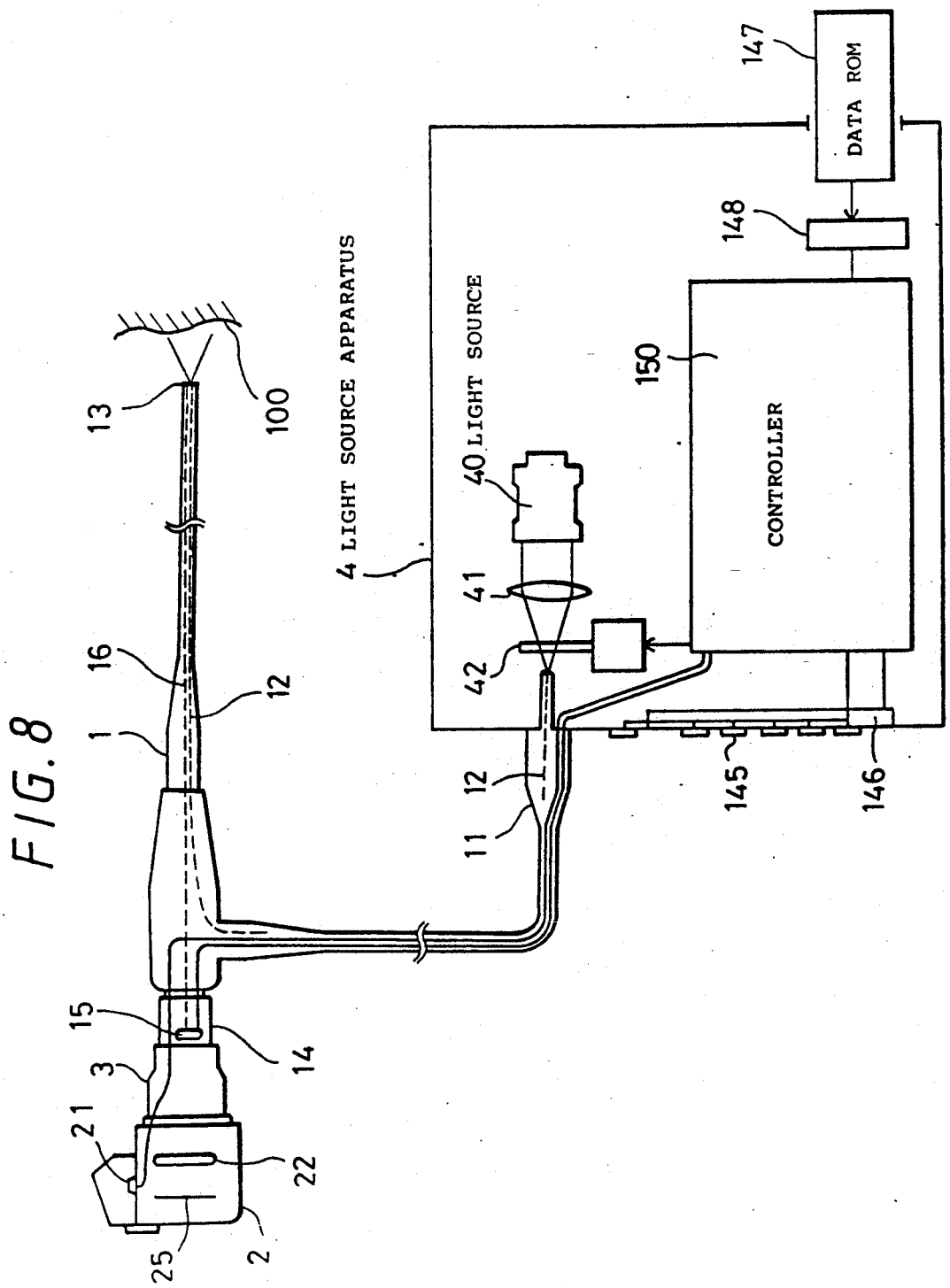
FIG. 8 shows a second embodiment of the light source apparatus for an endoscope according to the present invention.

Referring to FIG. 8, which illustrates another embodiment of Applicants' invention reference numeral 1 denotes an endoscope. A camera 2 is detachably attached to an eyepiece 14 of the endoscope 1 through a photographic adapter 3.

Reference numeral 4 denotes a light source apparatus, to which is detachably connected to a connector 11 of the endoscope 1. Illuminating light that is emitted from a light source 40 is condensed through a condenser lens 41, transmitted through a light guide fiber bundle 12 in the endoscope 1, and applied to an object 100 from the distal end 13 of an insert part of the endoscope 1. The reflected light from the object 100 is transmitted through an image guide fiber bundle 16 to expose the plane of a film 25 in the camera 2.

The exposure light quantity is controlled by a shutter (light source shutter) 42 which is provided in an illuminating light path inside the light source apparatus 4. A shutter 22 in the camera 2 is opened for a predetermined time, which is preferably about 0.25 sec, when a synchro switch 21 is turned on.

A light-receiving element 15 detects a brightness level of the exposure light that is applied to the plane of the film 25. The output ends of the synchro switch 21 and the light-receiving element 15 are connected to a controller 50 which is provided in the light source apparatus 4. In addition, input keys 145 and a display 146, which are provided on the front panel of the light source apparatus 4, are connected to the controller 150.

A read only memory (data ROM) 147, which is stored with data required to set an exposure index, is interchangeably provided with respect to the light source apparatus 4. Reference numeral 148 denotes a socket for detachably connecting the data ROM 147.

Figure 9:
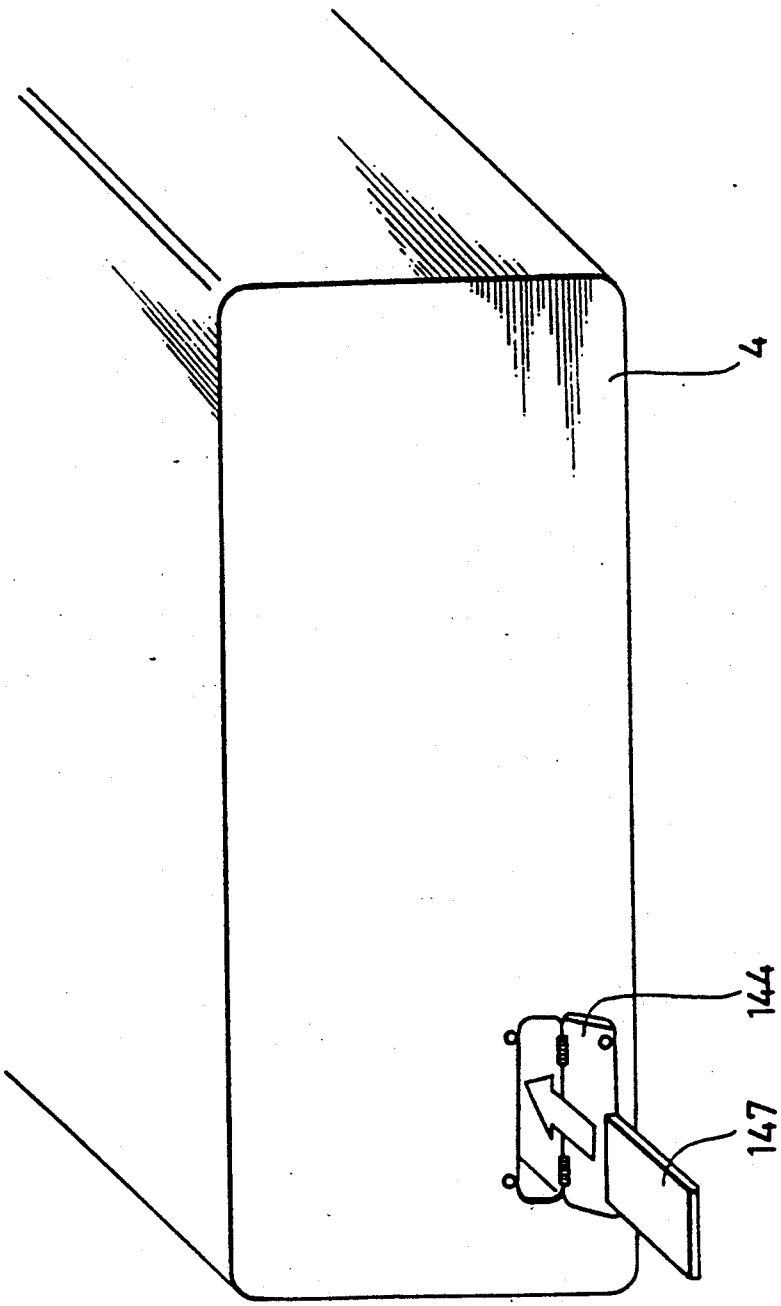
FIG. 9 is a rear perspective view of a light source apparatus in the second embodiment.

FIG. 9 shows a portion of the rear side of the light source apparatus 4 where the data ROM 147 is loaded. Reference numeral 144 denotes a lid.

Figure 10:
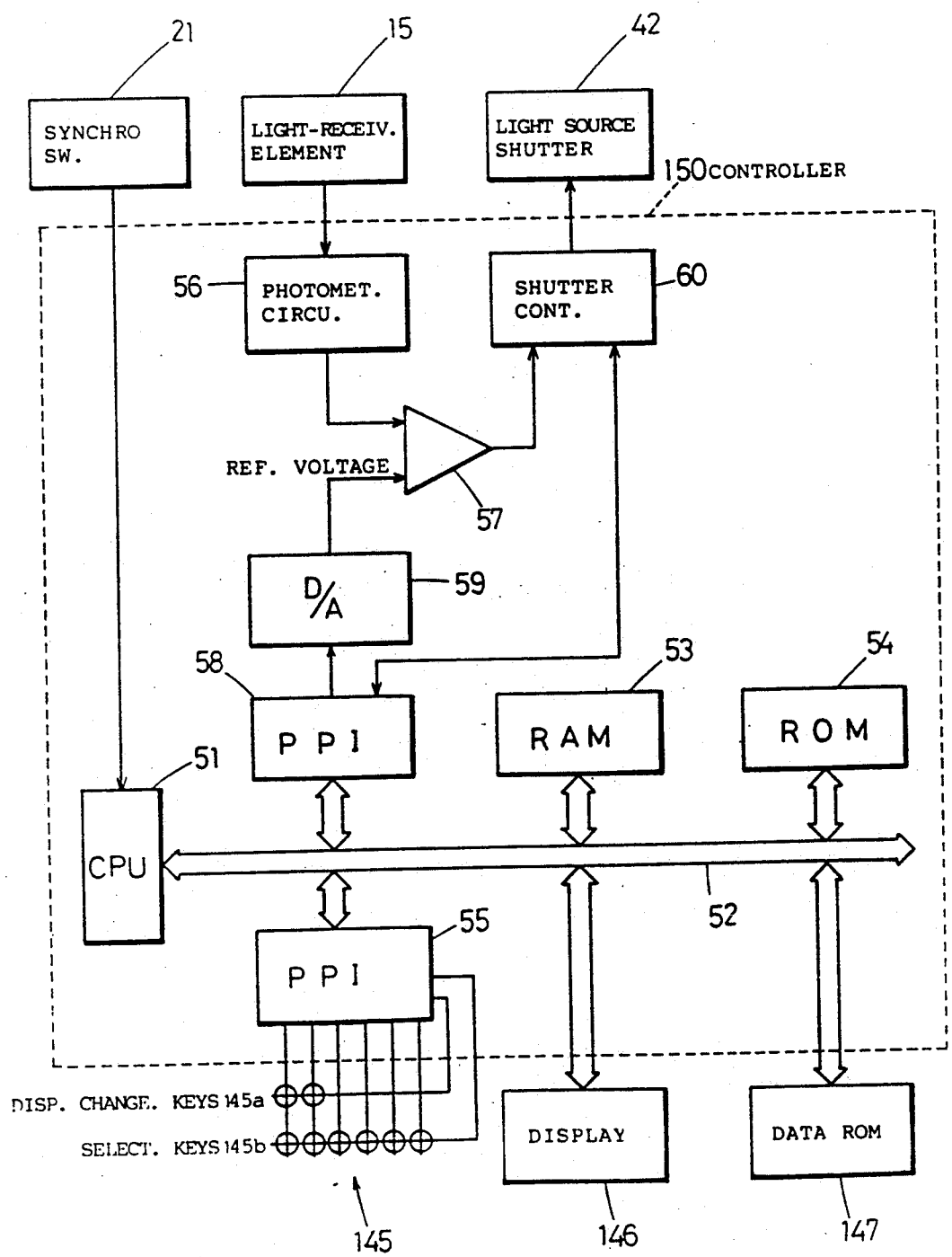
FIG. 10 is a circuit block diagram of the second embodiment.

Referring next to FIG. 10, which is a block diagram showing the arrangement of the controller 150, a random access memory (RAM) 53, a read only memory (ROM) 54, the display 146, the data ROM 147, and programmable interfaces 55 and 58 are connected to a system bus 52 which is in turn connected to a central processing unit (CPU) 51.

The CPU 51 is supplied with an interrupt signal which is outputted from the synchro switch 21. The input keys 145 include display changeover keys 145a and select keys 145b, which are connected to the system bus 52 through a first programmable interface (PPI) 55.

An output signal from the light-receiving element 15 is integrated in a photometric circuit 56 and then inputted to one input terminal of a comparator 57. The other input terminal of the comparator 57 is connected to the output terminal of a D/A converter 59 which converts a digital signal to an analog signal. The D/A converter 59 is connected to the system bus 52 through a second programmable interface (PPI) 58. The output terminal of the comparator 57 and the second PPI 58 are connected to a shutter control circuit 60 for controlling the operation of the shutter 42 in the light source apparatus 4.

Figure 11:
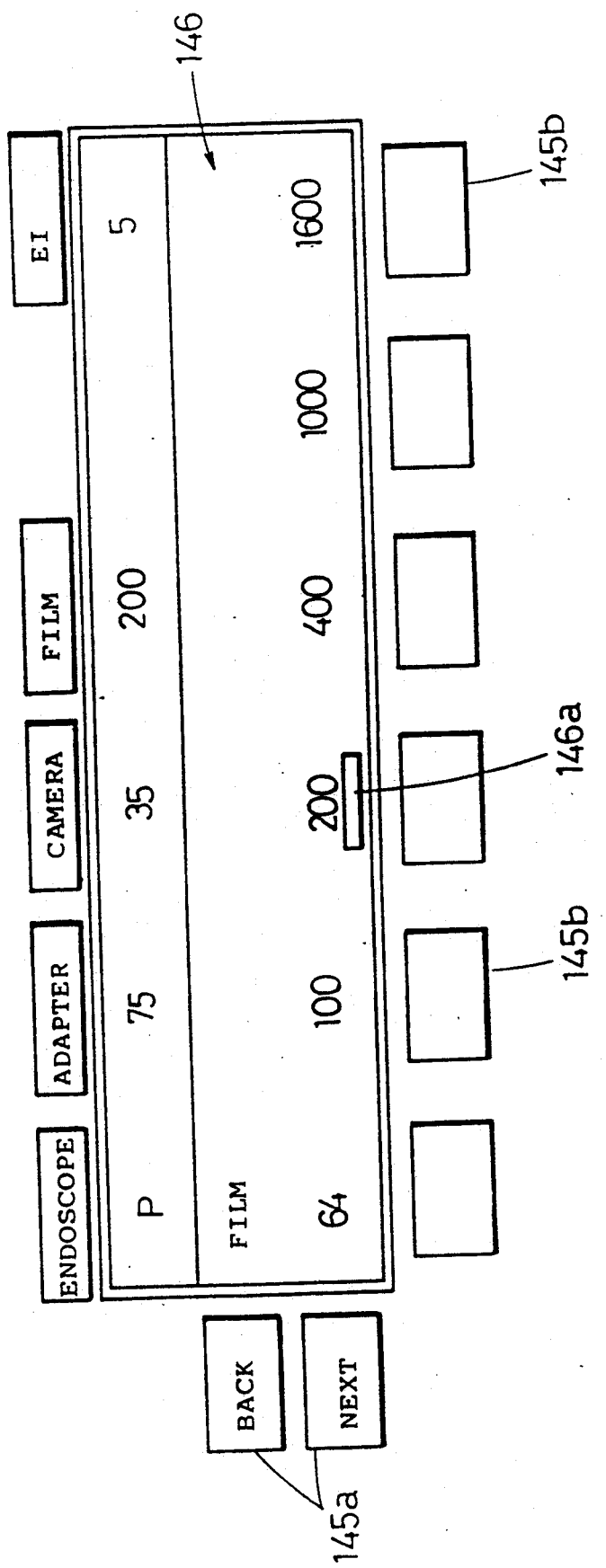
FIG. 11 is a front view of a panel in the second embodiment.

FIG. 11 shows the front panel of the light source apparatus 4, which is provided with the display 146 and the input keys 145 (145a and 145b).

At the upper side of the display 46 are displayed, from the left to the right, the types of endoscope, photographic adapter, camera and film, together with an exposure index to be set. One of these items is selected and displayed in the lower part of the display 146 by actuating the display changeover keys 145a. In the example shown in FIG. 11, "Film" is selected as an item and six different levels of sensitivity (ISO) are displayed.

Then, one of the optional conditions, i.e., data, concerning this item is selected by actuating one of the select keys 145b. Thus, the selecting operation is considerably easy. Reference numeral 146a denotes a light-emitting diode (LED) which is lit up at the position of the data selected. In the example shown in FIG. 11, a sensitivity of "200" is selected. The selected data is displayed in the upper part of the display 146.

Figure 12:
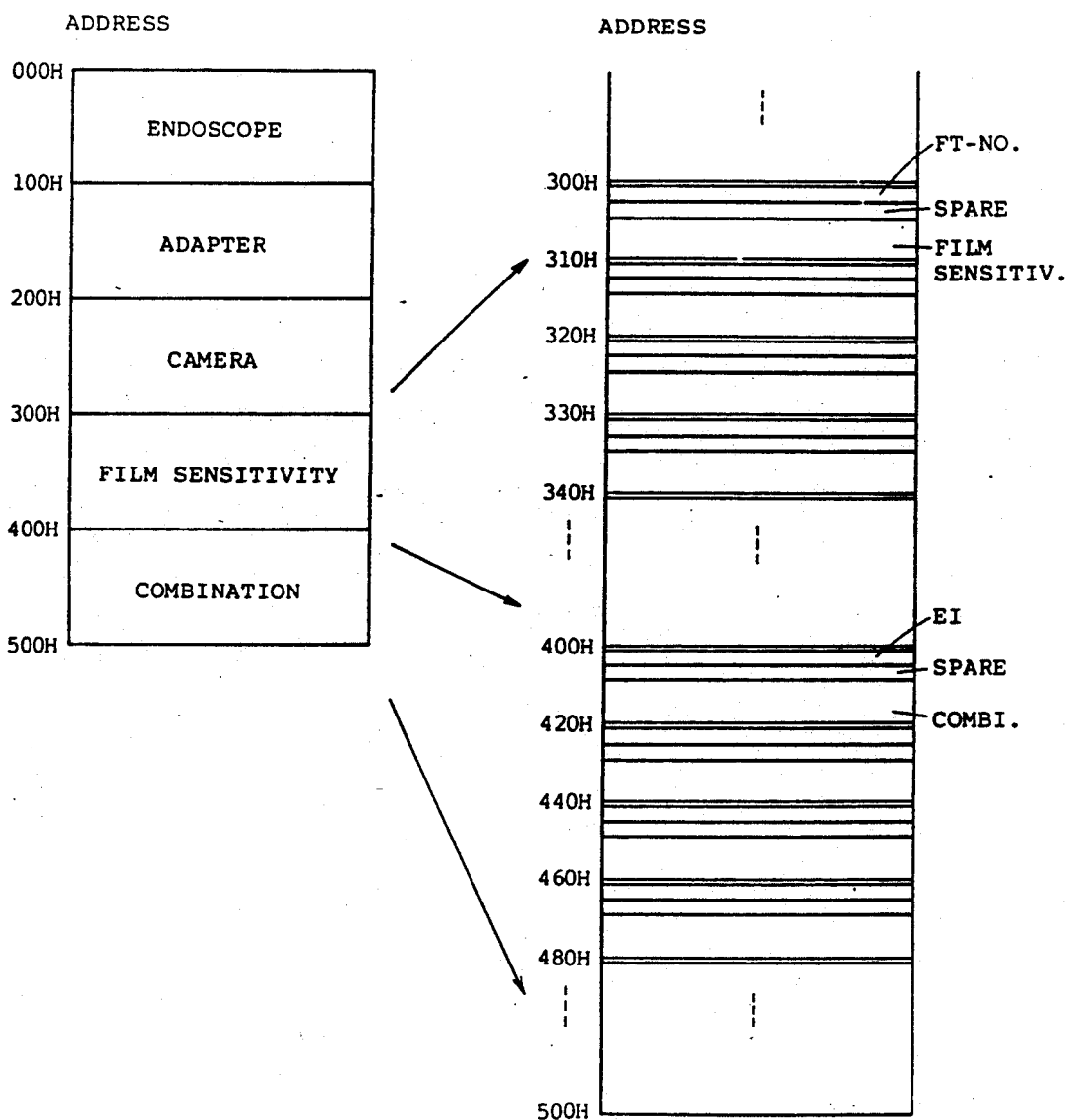
FIG. 12 is a schematic illustrating the contents of a data ROM in the second embodiment.

All the items and the contents thereof that are displayed on the display 146 are read from the data ROM 147. FIG. 12 exemplarily shows the contents of the data ROM 147. For example, each item is stored in one of the memory sections which are defined by dividing addresses every $100_H$, and each piece of the data is stored in one of the memory regions which are defined by subdividing each memory section every $10_H$.

In FIG. 12, which exemplarily shows the stored data concerning "Film", a film sensitivity and an FT-number which corresponds thereto are stored in each memory region in units of $10_H$ addresses. In spare regions, information other than sensitivities and FT-numbers is stored. It should be noted that FT-numbers are integral numbers for calculating the exposures index (EI) easily, which are adopted in this embodiment. The FT-numbers are set so that an exposure value difference of 1 EV is equivalent to 2 in terms of FT-numbers.

In addition, "Combination" is stored, as the last item in the data ROM 147. In this memory section are stored in pairs, combinations of an endoscope, a photographic adapter, a camera and a film, which are frequently used, and exposure indexes (FT-numbers) corresponding to these combinations. Accordingly, if these devices are used in any of the combinations stored, an optimal exposure index can be set instantaneously. Further, it is possible to cope with any combination of devices by replacing the data ROM 147 with a suitable one.

FIG. 13 shows the relationship between the exposure value and the exposure index, and FIG. 14 shows one example of the setting of FT-numbers.

As shown in FIG. 13, the exposure index (EI) for a standard exposure value is determined to be 5, and an exposure value difference of 1 EV is equivalent to 2 in terms of exposure index (EI).

Assuming that FT-values which are given by endoscopes, photographic adapters, cameras, films and exposure compensation values (EF) are FTs, FTa, FTc, FTf and FTe, respectively, the exposure index EI is given by $$EI = FTs + FTa + FTc + FTf + FTe - 11$$

It should be noted that the data shown in FIG. 14 is supplied from the data ROM 147. Accordingly, any exposure index can be set for any new data by replacing the data ROM 147.

FIG. 15 is a flowchart showing an exposure index setting process that is executed in the controller 150, in which S denotes Step.

Figure 16:
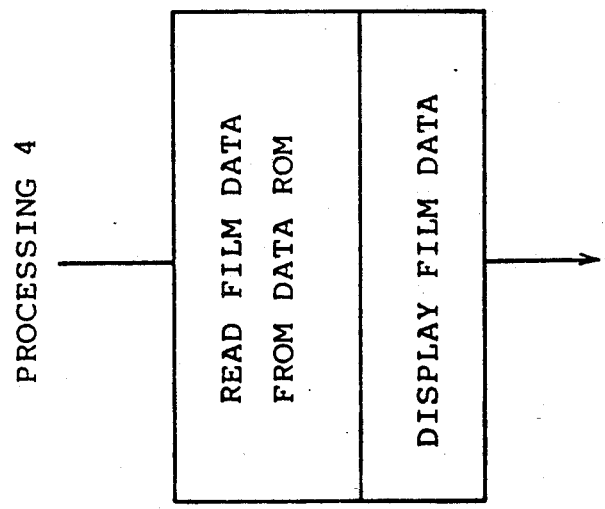

This process starts when an input operation is executed by actuating the input keys 145. It is first judged in S1 whether or not a display changeover key 145a has been actuated to execute the input operation. If YES, which item is being displayed is checked in S2 to S6. If the displayed item is "Film", for example, the process proceeds to S10, in which data concerning "Film" is read from the data ROM 147 and displayed on the display 146, as shown in FIG. 16, thus completing this processing.

If it is judged in S1 that the input operation has been executed through a key other than the display changeover keys 145a, that is, if a select key 145b has been actuated, the item that is being displayed at that time is checked in S12 to S16.

Figure 17:
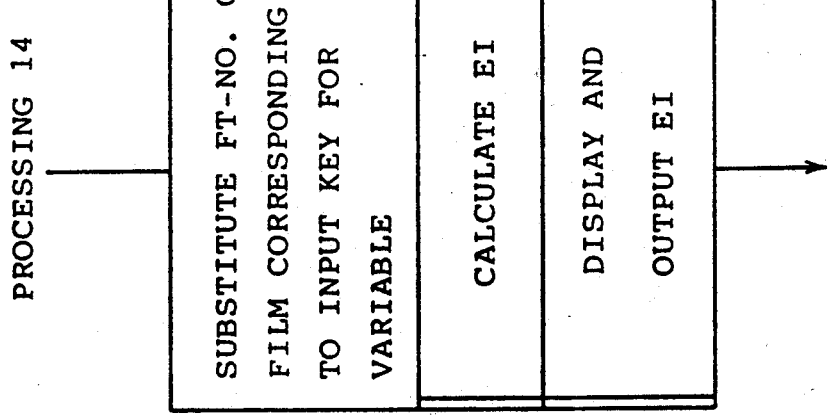

If the displayed item is "Film", for example, an FT-number corresponding to the film sensitivity concerned, which is selected by actuating a select key 145b, is substituted for the variable FTf in S20, as shown in FIG. 17. Then, an exposure index EI is calculated from the FT-value according to the above-described equation and displayed on the display 146 and further outputted from the second PPI 58 to the comparator 57 through the D/A converter 59, thereby controlling the operation of the shutter control circuit 60, and thus executing automatic exposure control with respect to the plane of the film 25 in the photographing operation.

It should be noted that, when the displayed item is any other than "Film", a similar processing is executed in S7, S8, S9 or S11, or S17, S18, S19 or S21 except that the item is different from that in S10 or S20.

Thus, an optimal exposure index is automatically set simply by selecting necessary data from among those which are read from the data ROM 147, and the exposure control with respect to the plane of the film 25 is executed on the basis of the set exposure index.

It should be noted that various kinds of IC card or other data storage means are usable as the data ROM 147 in the foregoing embodiment.

According to the present invention, conditions for setting an optimal exposure index are given from a data storage device which is interchangeably provided. Therefore, even when a new device or film having novel conditions is employed, an appropriate exposure index can be set simply by replacing the data storage device with a suitable one. Thus, it is possible to execute a photographing operation with a correct exposure at all times.

While the invention has been described by reference to a specific embodiment chosen for purposes of illustration, it should be apparent that numerous modifications could be made thereto by those skilled in the art without departing from the basic concept and scope of the invention.

We claim:

1. A light source apparatus for an endoscope, which has a light source for supplying exposure light for illuminating an object to the endoscope that is equipped with a photographing device when the object is photographed, comprising:

an exposure controller that controls a quantity of exposure light applied to a photographic plane in said photographing device;

a condition inputter than inputs various plural categories of conditions previous to the object being photographed for setting an exposure index which is used to determine said exposure light quantity, said categories of conditions being different from each other, said condition inputter having a memory for storing various conditions and a condition selector that selects appropriate conditions from among the various conditions stored in the memory, said condition inputter having a display for displaying various conditions stored in said memory, and a condition select switch for selecting appropriate conditions from among the various conditions displayed on said display; and an exposure index setter that calculates said exposure index from various of said plural categories of conditions which are inputted through said condition input means and output said exposure index to said exposure controller.

2. A light source apparatus for an endoscope, which has a light source for supplying exposure light for illuminating an object to the endoscope that is equipped with a photographing device when the object is photographed, comprising:

an exposure controller than controls a quantity of exposure light applied to a photographic plane in said photographing device;

a condition inputter that inputs various plural categories of conditions previous to the object being photographed for setting an exposure index which is used to determine said exposure light quantity, said categories of conditions being different from each other, said condition inputter having a memory for storing various conditions and a condition selector that selects appropriate conditions from among the various conditions stored in the memory, said condition inputter having a combination storer that stores a combination of conditions selected through said condition selector, and a combination selector that selects a combination of conditions in said combination storer; and an exposure index setter that calculates said exposure index from various of said plural categories of conditions which are inputted through said condition input means and outputs said exposure index to said exposure controller.

3. A light source apparatus for an endoscope, which has a light source for supplying exposure light for illuminating an object to the endoscope that is equipped with a photographing device when the object is photographed, comprising:

exposure control means for controlling the quantity of exposure light applied to a photographic plane in said photographing device;

condition input means for inputting various plural categories of conditions previous to the object being photographed for setting an exposure index which is used to determine said exposure light quantity, said categories of conditions being different from each other; and exposure index setting means for calculating said exposure index from various of said plural categories of conditions which are inputted through said condition input means and outputting said exposure index to said exposure control means, wherein said various plural categories of conditions that are inputted through said condition input means include the kinds of endoscope, camera and film.

4. A light source apparatus according to claim 3, wherein said various plural categories of conditions that are inputted through said condition input means further include the kind of adapter for connecting together a camera and an endoscope.

5. A light source apparatus according to claim 3, wherein said various plural categories of conditions that are inputted through said condition input means further include the degree of compensation for the exposure light quantity.

6. A light source apparatus for an endoscope, which has a light source for supplying light for illuminating an object to the endoscope that is equipped with a photographing device, comprising:

a data storer that stores data which is required to determine a quantity of exposure light applied to a photographic plane in said photographing device, said data storer being interchangeably provided and storing exposure indexes corresponding to at least two devices which are employed in a photographing operation, said data being used to select at least one device employed in said photographing operation;

a reader that reads said data from said data storer; and an exposure controller that controls said exposure light quantity using said data which is read by said reader.

7. A light source apparatus for an endoscope, which has a light source for supplying light for illuminating an object to the endoscope that is equipped with a photographing device, comprising:

a read only memory that stores data which is required to determine a quantity of exposure light applied to a photographic plane in said photographing device, said read only memory being interchangeably provided;

a reader than reads said data from said read only memory; and an exposure controller that controls said exposure light quantity using said data which is read by said reader.

* * * * *

UNITED STATES PATENT AND TRADEMARK OFFICE
CERTIFICATE OF CORRECTION

PATENT NO. : 5,184,159
DATED : February 2, 1993
INVENTOR(S) : Katsuhiko FURUYA et al.

It is certified that error appears in the above-indentified patent and that said Letters Patent is hereby corrected as shown below:

At column 10, line 29 (claim 7, line 10), change "than" to ---that---.

Signed and Sealed this

Sixth Day of June, 1995

Attest:

BRUCE LEHMAN

Attesting Officer

Commissioner of Patents and Trademarks